United States Patent
Rakitsch

Patent Number: 5,854,680
Date of Patent: Dec. 29, 1998

[54] PHOTOELECTRIC DENSITOMETER

[75] Inventor: Peter Rakitsch, Moosburg, Germany

[73] Assignee: Man Roland Druckmaschinen, Germany

[21] Appl. No.: 846,122

[22] Filed: Apr. 25, 1997

[30] Foreign Application Priority Data

Apr. 27, 1996 [DE] Germany ............ 196 17 009.5

[51] Int. Cl.⁶ .................. G01J 3/51; G01N 21/25
[52] U.S. Cl. ............ 356/406; 356/419; 356/425; 101/DIG. 45
[58] Field of Search ................. 356/402, 405, 356/406, 407, 416, 419, 425; 101/DIG. 45

[56] References Cited

U.S. PATENT DOCUMENTS

| | | | |
|---|---|---|---|
| 4,003,660 | 1/1977 | Christie et al. | |
| 4,681,454 | 7/1987 | Breemer | 356/402 |
| 4,917,500 | 4/1990 | Lugos | 356/406 |
| 5,117,101 | 5/1992 | Moore et al. | 356/405 |
| 5,129,726 | 7/1992 | Nielsen | 356/406 |

FOREIGN PATENT DOCUMENTS

| | | |
|---|---|---|
| 0 011 376 | 10/1983 | European Pat. Off. |
| 38 30 731 | 3/1990 | Germany . |
| 41 20 749 | 2/1992 | Germany . |
| 43 14 219 | 11/1994 | Germany . |

*Primary Examiner*—F. L. Evans
*Attorney, Agent, or Firm*—Leydig, Voit & Mayer, Ltd

[57] ABSTRACT

A description is given of a photoelectric measuring device by means of which the light reflected from a measuring point on a printed product is detected, and the corresponding measured signals are processed for the purpose of indicating quality data. A measuring instrument of this type, having at least one illumination device and measuring channels, is an improvement over the prior art in order to expand its possible uses, with a construction which is cost-effective and stable when handled. In accordance with the invention, this is achieved with an illumination device which has a spectral intensity distribution which corresponds to the number of spectral ranges provided for the irradiation of the measuring point. The light from the sequentially drivable illumination devices irradiates the measuring point. The light reflected from the measuring point is detected and converted into a reflective signal which is processed to determine ink density values. The photoelectric measuring device is designed, in particular, as a densitometer, preferably being made using light-emitting diodes (LEDs). Interference filters are additionally used in order to match the spectral intensities of the diodes to the spectral ranges which are provided for obtaining ink density values.

20 Claims, 3 Drawing Sheets

PHOTOELECTRIC DENSITOMETER

TECHNICAL FIELD

The invention relates to a photoelectric measuring devices having a plurality of illumination sources and, in particular, to such devices having sequentially activated illumination sources exposing areas to be measured to light of different spectral intensity.

BACKGROUND OF THE INVENTION

Most photoelectric measuring devices are used in order to check the quality of printed products. One such device is a densitometer in which the light reflected from a measuring point is photoelectrically converted to a reflection value. An ink density value is determined from the logarithm of this reflection value. The ink density value for a given printing ink is detected in a spectral range which is complementary to the ink color. In other words, the spectral range of the color having the lowest reflectance is used to derive an ink density.

The optical structure of a densitometer essentially comprises at least one illumination device for irradiating the measuring point on the printed product to radiation. Additional configurations are possible using one or more measuring channels, each measuring channel having one or more photoelectric converters and corresponding filter elements connected upstream. The spectral transmission properties of the filters placed in the respective measuring channels are configured in accordance with the ink density value to be derived.

For example, Tobias, EP 0 011 376 B1, published Oct. 12, 1983, describes a densitometer which has, in the measuring head, an illumination beam path and a light source as well as three simultaneously effective measuring channels. For the purpose of deriving the appropriate ink density values in evaluation electronics connected downstream, a filter is place in each of the measuring channels for the colors cyan, magenta and yellow, which are used in printing. These filters permit red, green, and blue light to pass through to the photoelectric converter placed in each of the respective measuring channels for the colors cyan, magenta and yellow. The ink density values are determined from the detected reflected light. By processing the reflection values obtained via the three measuring channels and referencing stored values, it is also possible to determine the color of a printed measuring area.

Christie, Jr., U.S. Pat. No. 4,003,660, issued Jan. 18, 1977, describes a multi-color printing press on-line densitometer that has two illumination channels in order to irradiate the measuring fields of a printing control strip. A section of the control strip is imaged onto a plane which has a plurality of photoelectric converters. Although the illumination of the measuring field area to be measured is carried out here by two illumination devices, the latter are of mutually identical design.

In the case of the color measuring instruments which are nowadays being increasingly used in the printing industry in order to detect and derive so-called standard calorimetric values, it is known to use light sources that simulate different illumination situations. This is accomplished either in an illumination channel by means of filter devices which can be switched in and out, or by means of a plurality of illumination channels having having different spectral characteristics. In the case of such color measuring instruments, filters are provided on the receiver side in order to weigh the light reflected from a measuring field in a spectrally different manner according to a standardized measuring rule. The optical structure of such color measuring instruments is correspondingly complex.

In addition to densitometers having a plurality of simultaneously operating measuring channels, densitometers have also been disclosed that have a photoelectric converter in which different filters for the spectral evaluation of the light reflected from the measuring point can be connected in front of the receiver sequentially one after another. However, sensitive mechanical devices of this nature likewise complicate the structure of such measuring heads. Furthermore, in the case of a plurality of filters which have to be connected sequentially in front of a photoelectric converter, it is necessary for the transmission ranges of the filters to be matched to one another. Likewise, known in the case of reflection measuring heads is the use of a plurality of photoelectric converters in conjunction with mirror systems. The reflected light is spectrally divided by these mirrors and fed to the individual converters. The disadvantage of this arrangement is that the intensity of the light reflected from the measuring point is additionally reduced by optical losses. Furthermore, a disadvantage of known measuring instruments which have incandescent lamps for illumination is that these lamps have a higher emission in the IR spectral range than in the visible spectral range. Additional IR filters are consequently necessary in order to influence this IR range.

Lugos, U.S. Pat. No. 4,917,500, describes a color sensor system for the recognition of objects with colored surfaces in which there is provided a number of illumination arrangements sequentially drivable and light-emitting in different wavelength ranges. The light reflected from the measuring surface is fed to a photoelectric receiver and processed by an evaluating and processing unit for the formation of displayable measurement values.

Böner, DE 41 20 749 Al, published Feb. 20, 1992, describes a process for the point-for-point determination of a spectral remission function by means of an optoelectronic measuring head. Optoelectronic radiation transmitters are arranged in a dome-shaped housing unit, with each transmitter occupying an equal angle to a measuring point. Here, too, the individual illumination arrangements emitting in different spectral ranges are sequentially driven, so that, for example, the CIE color-measurement numbers are determinable.

Morgenstern, DE 43 14 219 Al, published Nov. 3, 1994, describes an arrangement for the point-by-point measurement of the remission. Radiation concentrators are arranged according to the radiation sources, each of which have the form of a truncated cone and consist of a highly refractive glass transformed by a low-refracting glass, so that the radiation is concentrated essentially by total reflection onto a small section of the measuring surface.

DE 34 18 839 Al describes an apparatus for colorimetry/photometry which has a number of illumination arrangements emitting in different spectral ranges. In these arrangements glass filters restrict the wavelength ranges of the light sources. Furthermore, the light of a light source is conducted over light-conducting cables to the input optic of the measuring unit.

Breemer, U.S. Pat. No. 4,681,454 describes an apparatus for the determination of color differences having a number of illumination arrangements,which are individually drivable and emitting in different wavelength ranges. The light of these illumination arrangements is fed over a measurement surface to a photoelectric converter. A second photoelectric converter is provided to which the light emitted directly from the illumination arrangements is suppliable.

Kipphan, DE 38 30 731 Al, published Mar. 22, 1990, describes a device for color measurement which has, in the measuring head, a three-color simultaneous measuring head used for the densitometric measurement and an additional three-color simultaneous measuring head integrated for the calorimetric meausurement. In such an arrangement, there can be carried out at will measuring data for the execution of color-control or color-regulating processes according to a calorimetric or a densitometric measuring principle.

SUMMARY OF THE INVENTION

The primary object of the invention is to provide a new photoelectric measuring device which is as simple and cost-effective as possible, while avoiding the aforementioned disadvantages. It is a further object of the invention to expand the field of use of a measuring instrument which is, in particular, designed as a densitometer, and providing a photoelectric measuring device with an increased measuring and processing accuracy over known devices.

To this end, according to the primary aspect of the invention, disclosed hereinafter is a new photoelectric measuring device having a plurality of illumination sources, and in particular, sequentially activated illumination sources exposing the measuring area to light of different spectral intensity. The spectral intensity distribution of these illumination sources is selected in accordance with the regulation for the spectral weighing of the light reflected from the measuring point. In the case of a measuring head which is designed as a densitometer, three illumination channels are provided. Each one of the channels irradiates the measuring point with blue, green or red light. By comparison with the structure of conventional densitometers that generate radiation in a very broad range in order to illuminate the measuring point which results in the generation of high heat in the case of thermal light sources (i.e., incandescent lamps), this invention has the advantage of avoiding thermal dissipation issues and the additional construction efforts necessary for prior designs. In the case of illumination with LEDs, it is possible to dispense, in particular, with IR blocking filters.

In a densitometer embodiment in accordance with the invention, light-emitting diodes (LEDs) are used. The LEDs can additionally have interference filters connected in front of them. By means of a controller connected upstream, the LEDs of the yellow, magenta and cyan channel are sequentially switched on and off one after another for a short time duration, with the result being that the corresponding reflectances of the measuring point occur serially at the photoelectric converter. An amplification and evaluation circuit, connected downstream of the photoelectric converter, receives the corresponding reflectance signals for the cyan, magenta, yellow and the black channel and converts them into ink density units which can be used by a device connected downstream. Additionally, a dark phase can likewise be serially prescribed by the controller, such that within this dark phase, the photoelectric converter receives no light emitted by one of the illuminating LEDs via the measuring point. Within this dark phase, the signal produced by the photoelectric converter can be used by the amplification and evaluation unit as an offset, and processed for the indication of the measured values.

The clock frequency with which the individual LEDs are sequentially driven may be a few kilohertz. The limit of the clock frequency is essentially determined by the maximum admissible clock frequency of the elements comprising the amplification and evaluation unit (i.e., an A/D converter or switchable amplifier).

In keeping with the invention, in addition to the photoelectric converter, a second photoelectric receiving unit 5a, designed in particular as an SI photodiode, is exposed directly to the light of the LEDs illuminating the measuring point. By means of this second photoelectric receiving unit, the direct irradiation intensity of the individual LEDs is detected, so that any brightness fluctuations of the LEDs can be taken into account and corrected in the amplification and evaluation unit in order to derive exact measured values.

In another embodiment of the invention, the photoelectric measuring device has light guide devices by which the differently colored light of the individual LEDs can be directed onto the measuring point for the purpose of illumination in accordance with the selected measuring rule. Use can preferably be made here of a multi-armed light guide having a plurality of light input coupling surfaces and one light output coupling surface. This light guide may have a further light exit surface, via which the light from the LEDs can be fed directly to the additional photoelectric receiving unit (i.e., the SI photodiode) described above. The light reflected from the measuring point may likewise be fed via a separate light guide to the photoelectric converter connected upstream of the amplification and evaluation unit. Suitable coupling optics are used for coupling the radiation into and out of the light guide.

BRIEF DESCRIPTION OF THE DRAWINGS

Other objects and advantages of the invention will become apparent upon reading the attached detailed description and upon reference to the drawings in which.

While the invention has been described in connection with certain preferred embodiments, it will be understood that there is no intention to limit the invention to the embodiments shown, but it is intended, on the contrary to cover the various alternative and equivalent constructions included within the spirit and scope of the appended claims.

DETAILED DESCRIPTION OF THE INVENTION

Figure 1:
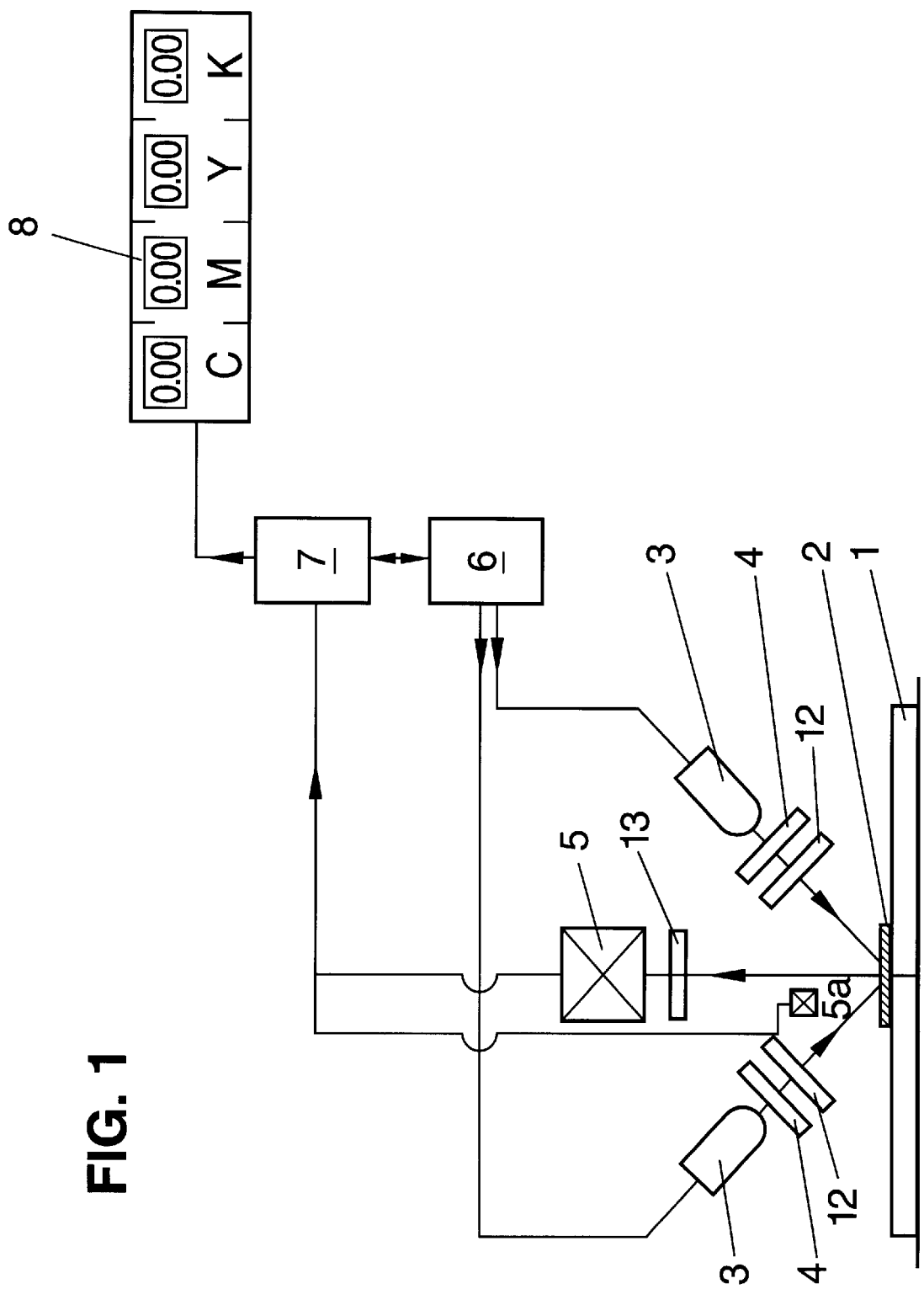
FIG. 1 is a schematic diagram illustrating the design of an embodiment of the invention.

Turning now to the drawings, there is shown in FIG. 1 the basic construction of the measuring device. In a housing (not shown), three light-emitting diodes (LEDs) 3 are arranged around a central photoelectric converter 5 such that the irradiation by the LEDs 3 of a measuring point 2, which is located on a printed sheet 1, is carried out in each case at 45 degrees to the surface normal, and the light reflected from the measuring point 2 on the sheet 1 is received by the photoelectric converter 5 in the direction of the surface normal. The LEDs 3 and the photoelectric converter 5 are set into holes drilled in the housing (not shown), so that the photoelectric converter 5 is shadowed to the greatest possible extent against scattered light caused by ambient brightness.

Figure 2:
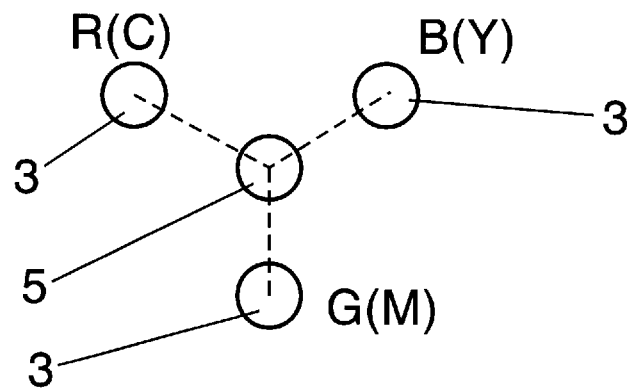
FIG. 2 is a schematic diagram of a cross-section of FIG. 1 illustrating the relative placement of three illumination sources surrounding the photoelectric converter.

The relative placement of the three LEDs 3 surrounding the photoelectric converter 5 is best illustrated in FIG. 2. The three LEDs 3 are assigned to the red (R), blue (B), and green (G) channels, which correspond to the individual printing inks cyan (C), yellow (Y), and magenta (M). The LEDs 3 are arranged to be offset by 120 degrees from one another and distributed about the photoelectric converter 5, which is located directly above the measuring point 2.

Each of the LEDs 3 is of a commercially available design, having radiation properties that permit determination of ink density values as described herein. For instance, the radiation properties of the LED 3 for the red (R) channel allows the ink density value for the printing ink cyan (C) to be determined. Specifically, the LED 3 for the red (R) channel has a spectral intensity distribution essentially in the longwave red range. Similarly, the radiation intensity of the diode 3 assigned to the blue channel (B) for the purpose of obtaining an ink density value for yellow (Y) has a maximum spectral intensity in the blue range, and the light-emitting diode 3 of the green channel G for the printing ink magenta (M) has an intensity maximum in green range.

Returning now to FIG. 1, additionally connected upstream of the individual LEDs 3 are narrow-band interference filters 4, so that the light emitted by the LEDs 3 is matched exactly to the spectral condition for deriving ink density values. In particular, those spectral regions that are not suitable for the purpose of obtaining ink density values are blanked out from the spectral intensity distributions of the LEDs 3. In order to suppress the surface gloss, especially in the case of a freshly printed sheet 1, a polarizer (12) is arranged between the interference filters 4 and the measuring point (2), and an analyzer (13) is arranged between the photoelectric converter 5 and the measuring point (2).

Each of the LEDs 3 is individually connected to a controller 6, via which sequential driving of the LEDs is carried out. Controller 6 comprises conventional components and devices such as a clock and counters. Alternatively, it may comprise a microprocessor controller appropriately programmed to generate the sequential illumination of the LEDs 3. For example, first LED 3 of the red (R) channel, then LED 3 of the green (G) channel, then LED 3 of the blue (B) channel are successively activated by the controller 6 for a short time interval. Additionally, a dark phase may also be provided, in which the controller 6 drives none of the three LEDs 3. As a result of this sequential driving of the three LEDs 3 by the controller 6, the photoelectric converter 5 receives the light reflected from the measuring point 2 in the red, green and blue range (R, G, B), one after another.

The photoelectric converter 5 is connected to an amplification and evaluation unit 7, by means of which the electric variables corresponding to the reflection intensities are processed. By means of processing the reflectance values of the red (R), green (G) and blue (B) channels, an ink density value for the printing ink black (K) may be derived in a well known manner. The amplification and evaluation unit 7 is connected to controller 6 to synchronize its processing of the reflectance values with the sequential illumination of the LEDs 3. The amplification and evaluation unit 7 comprises conventional components and devices such as A/D converters, switchable amplifiers, a microprocessor controller appropriately programmed, and other readily available descrete components. Connected downstream of the amplification and evaluation unit 7 is an indicator device 8 by means of which the ink density values for the printing colors cyan (C), magenta (M), yellow (Y), and black (K) can be indicated. Indicator 8 comprises conventional components and devices such as an LCD or LED display and controller. In addition, the amplification and evaluation unit 7 can be connected to printing machine control devices (not shown).

Figure 3:
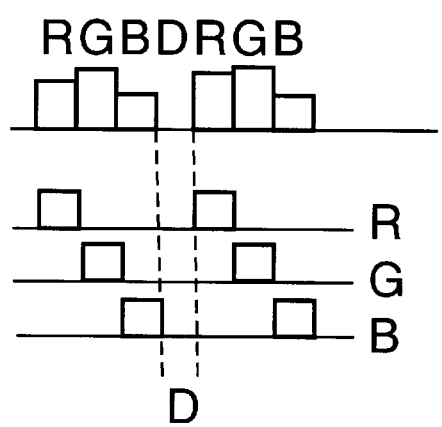
FIG. 3 is a timing diagram for an embodiment using three light sources and a dark phase, illustrating the period for which each light source is illuminated and exemplary reflectance values.

Turning now to FIG. 3, shown in principle is an exemplary timing profile of the three driving processes for the red (R), green (G) and blue (B) channels, which are offset in relation to one another. The dark phase D, which can be predetermined by the controller 6, is likewise indicated. Also shown is an exemplary timing profile of the reflectance values occurring in red (R), green (G) and blue (B) channels. These values are detected by the amplification and evaluation unit in accordance with the sequencing of the LEDs 3 determined by the controller 6.

Figure 4:
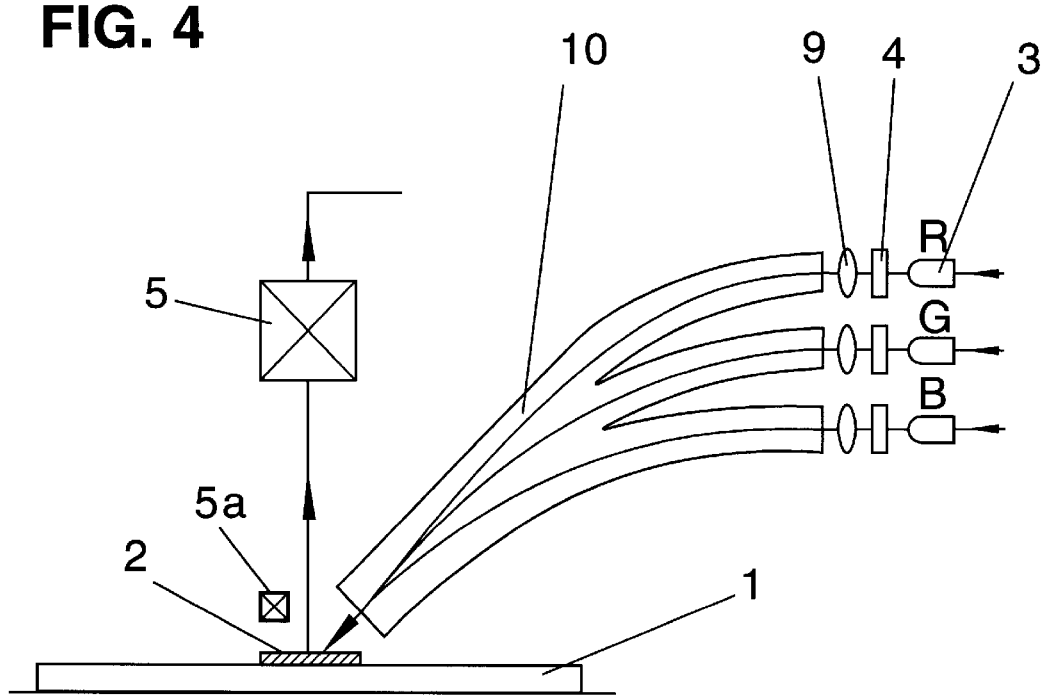
FIG. 4 is a schematic diagram of the optical design of an embodiment of the invention having having a light guide for illiminating the measuring point.

Turning now to FIG. 4, shown is another optical arrangement in accordance with the invention. A light guide 10 is used for illuminating the measuring point 2 on the sheet 1. The three LEDs 3 corresponding to the red (R), green (G) and blue (B) channels are each assigned a light input coupling point on the light guide 10. Additional coupling optics 9 are connected upstream as shown. Likewise, LEDs 3 are assigned additional interference filters 4, by means of which the spectral matching of the light emitted by the LEDs 3 is carried out as previously described.

As represented in FIG. 4, the light guide 10 has three arms with light input coupling points, which are assigned to the corresponding LEDs 3. The light from the LEDs 3 which is captured by the light input coupling points is lead to the measuring point 2 of the sheet 1 in accordance with the illumination geometry provided. A so-called 45°/0° geometry is shown. Accordingly, the light guide 10 has a light exit surface which is assigned to the measuring point 2. The light which is reflected from the measuring point 2 in accordance with the sequential driving of the LEDs 3 is fed to the photoelectric converter 5. As described in relation to the embodiment of FIG. 1, imaging means (e.g., polarizer, analyzer) can be optionally interposed in the light path.

Figure 5:
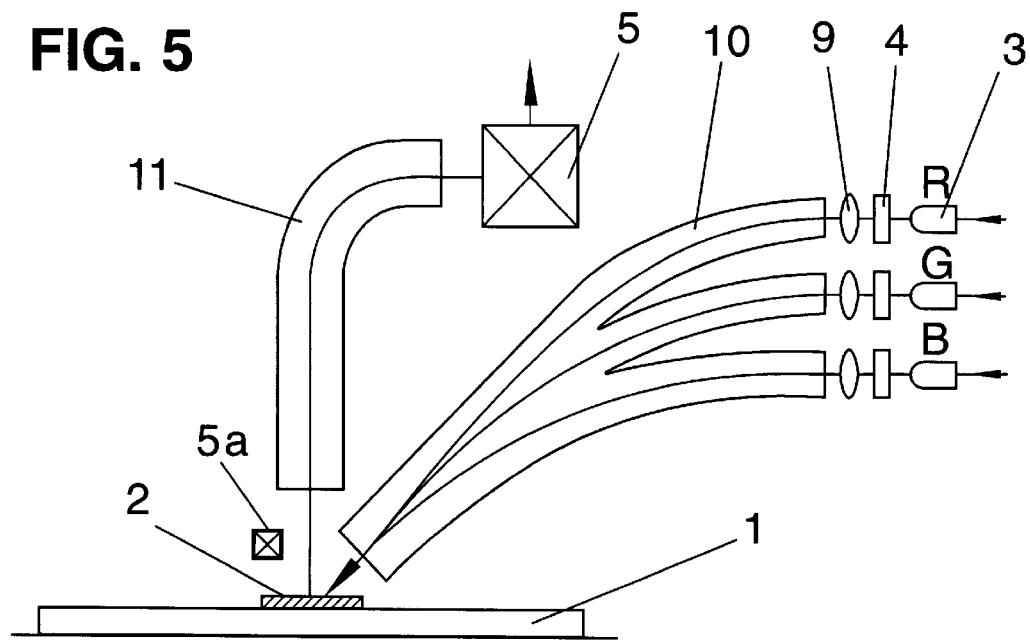
FIG. 5 is the schematic diagram shown in FIG. 4 with the addition of a light guide device for directing light reflected from the measuring point to the photoelectric converter.

Turning now to FIG. 5, a light guide 11 is likewise provided in accordance with the invention for exposing the photoelectric converter 5 to the light reflected from the measuring point 2 in accordance with the sequential driving of the LEDs 3. Here too, the representation of the light guide 11 is purely in principle as the actual embodiment depends on the envisaged dimensions of the measuring head to be provided.

From the foregoing, it will be appreciated that a new photoelectric measuring device with a plurality of illumination sources sequentially activated to expose the measuring area to light of different spectral intensity has been described. Using the simple and cost-effective measuring device of the invention, the ink density values for the printing ink colors cyan (C), magenta (M), yellow (Y), and black (K) can readily determined and indicated, and provided to downstream devices.

I claim:

1. A method of measuring a density of ink at an area of a printed product comprising the steps of generating a predetermined sequence of incident beams of light having different spectral intensity distributions; irradiating the measuring area with the incident beams of light, a portion of every incident beam of light being reflected by the measuring area to produce reflected beams of light; collecting the reflected beams of light; generating reflectance signals, each reflectance signal being correlated to an intensity of a respective reflected beam of light; generating from the reflectance signals an ink density signal; and generating at least one dark phase during the sequence of incident beams of light in which the measuring area is not irradiated with the incident beams of light, a dark phase reflectance signal being generated during the at least one dark phase and used as an offset value for generating the ink density signal.

2. The method of claim 1, wherein the step of generating a predetermined sequence of incident beams of light having different spectral intensity distributions comprises the steps of irradiating the measuring area with an incident beam of light having a spectral intensity distribution in a red wavelength range for obtaining ink density values of the color cyan used in printing, irradiating the measuring area with an incident beam of light having a spectral intensity distribution in a green wavelength range for obtaining ink density values of the color magenta used in printing, and irradiating the measuring area with an incident beam of light having a spectral intensity distribution in a blue wavelength range for obtaining ink density values of the color yellow used in printing.

3. The method of claim 2, wherein the step of generating a predetermined sequence of incident beams of light having different spectral intensity distributions further comprises the steps of collecting the incident beams of light and generating incidence signals, each incidence signal being correlated to an intensity of a respective incident beam of light; and wherein the step of generating from the reflectance signals an ink density further comprises the step of adjusting the ink density based on the value of the dark phase reflectance signal.

4. A photoelectric densitometer for measuring an area of a printed product, comprising: a plurality of illumination devices for irradiating the measuring area with incident beams of light, a portion of every incident beam of light being reflected by the measuring area to produce reflected beams of light; a photoelectric converter collecting the reflected beams of light and generating reflectance signals, each reflectance signal being correlated to an intensity of a respective reflected beam of light; an evaluator, connected to the photoelectric converter, for evaluating the reflectance signals to generate an ink density signal; a controller connected to the plurality of illumination devices for activating each one of the plurality of illumination devices in a predetermined sequence, at least one of the plurality of illumination devices generating a light having a different spectral intensity distribution than the other individual illumination devices; wherein the controller sequentially activates the individual illumination devices with at least one dark phase during which the measuring area is not irradiated with the incident beams of light, a dark reflectance signal being generated during the at least one dark phase and used as an offset by the evaluator when generating the ink density signal.

5. The photoelectric densitometer of claim 4, wherein the plurality of illumination devices comprise at least a first, a second, and a third individual illumination device for respectively irradiating the measuring area with incident beams of light having a spectral intensity distribution in a red, green and blue wavelength range for obtaining ink density values of the colors cyan, magenta, and yellow used in printing.

6. The photoelectric densitometer of claim 4, wherein the plurality of illumination devices comprise light-emitting diodes (LEDs) of different spectral intensity distribution.

7. The photoelectric densitometer of claim 4, wherein the plurality of illumination devices further comprise interference filters.

8. The photoelectric densitometer of claim 4, wherein the plurality of illumination devices further comprise light guides.

9. The photoelectric densitometer of claim 8, further comprising a multi-armed light guide having a light input coupling corresponding to each of the plurality of illumination devices and having a light output coupling point facing the measuring area.

10. The photoelectric densitometer of claim 9, further comprising a light guide directing the reflected beams of light to the photoelectric converter.

11. The photoelectric densitometer of claim 4, further comprising a second photoelectric converter collecting the incident beams of light, and generating incidence signals, each incidence signal being correlated to an intensity of a respective incident beam of light, the second photoelectric converter connected to the evaluator, wherein evaluator evaluates the incidence signals for adjusting the ink density signals.

12. The photoelectric densitometer of claim 4, further comprising a polarizer disposed between the plurality of illumination devices and the measuring area whereby the incident beams of light from the plurality of illumination devices pass through the polarizer; and an analyzer for the suppression of surface gloss arranged between the measuring area and the photoelectric converter.

13. The photoelectric densitometer of claim 5, wherein the plurality of illumination devices include: light-emitting diodes (LEDs) of different spectral intensity distribution; interference filters; light guides including a multi-armed light guide having a light input coupling corresponding to each of the plurality of illumination devices and having a light output coupling point facing the measuring area.

14. The photoelectric densitometer of claim 13, further comprising: a second photoelectric converter collecting the incident beams of light, and generating incidence signals, each incidence signal being correlated to an intensity of a respective incident beam of light, the second photoelectric converter connected to the evaluator, wherein evaluator evaluates the incidence signals for adjusting the ink density signals; a light guide directing the light reflected off the measuring area to the photoelectric converter; a polarizer disposed between the plurality of illumination devices and the measuring area whereby the incident beams of light from the plurality of illumination devices pass through the polarizer; and an analyzer for the suppression of surface gloss arranged between the measuring area and the photoelectric converter.

15. A photoelectric densitometer for measuring an area of a printed product, comprising: a plurality of illumination devices, including light-emitting diodes (LEDs) of different spectral intensity distribution, at least one illumination device generating a light having a different spectral intensity distribution from the other illumination devices, for irradiating the measuring area with incident beams of light, a portion of every incident beam of light being reflected by the measuring area to produce reflected beams of light; a controller connected to the plurality of illumination devices for sequentially activating the plurality of illumination devices, wherein there is at least one dark phase during which the measuring area is not irradiated with any incident beams of light; a photoelectric converter collecting the reflected beams of light and generating reflectance signals, each reflectance signal being correlated to an intensity of a respective reflected beam of light, a dark phase reflectance signal being generated during the at least one dark phase; an evaluator, connected to the photoelectric converter, for evaluating the reflectance signals to generate an ink density signal, the dark phase reflectance signal being used as an offset by the evaluator when generating the ink density signal; a second photoelectric converter collecting the incident beams of light, and generating incidence signals, each incidence signal being correlated to an intensity of a respective incident beam of light, the second photoelectric converter connected to the evaluator, wherein evaluator evaluates the incidence signals for adjusting the ink density signal.

16. The photoelectric densitometer of claim 15, wherein the plurality of illumination devices further comprise: light guides including a multi-armed light guide having a light input coupling corresponding to each of the plurality of illumination devices and having a light output coupling point facing the measuring area.

17. The photoelectric densitometer of claim 16, further comprising a light guide directing the reflected beams of light to the photoelectric converter.

18. The photoelectric densitometer of claim 16, further comprising: a polarizer disposed between the plurality of illumination devices and the measuring area whereby the incident beams of light from the plurality of illumination devices pass through the polarizer; and an analyzer for the suppression of surface gloss arranged between the measuring area and the photoelectric converter.

19. The photoelectric densitometer of claim 16, wherein the plurality of illumination devices further comprise interference filters.

20. The photoelectric densitometer of claim 17, wherein the plurality of illumination devices further comprise interference filters.

* * * * *